(12) United States Patent
Smith

(10) Patent No.: US 12,256,968 B2
(45) Date of Patent: Mar. 25, 2025

(54) VARIABLE PITCH TAPERED COMPRESSING SCREW FOR DYNAMIC COMPRESSION

(71) Applicant: Acumed LLC, Hillsboro, OR (US)

(72) Inventor: Terrence Chadwick Smith, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 191 days.

(21) Appl. No.: 17/522,289

(22) Filed: Nov. 9, 2021

(65) Prior Publication Data

US 2022/0142691 A1 May 12, 2022

Related U.S. Application Data

(60) Provisional application No. 63/112,425, filed on Nov. 11, 2020.

(51) Int. Cl.
*A61B 17/86* (2006.01)
*A61B 17/68* (2006.01)

(52) U.S. Cl.
CPC ........ *A61B 17/8685* (2013.01); *A61B 17/863* (2013.01); *A61B 2017/681* (2013.01); *A61B 2017/8655* (2013.01)

(58) Field of Classification Search
CPC .............. A61B 17/8685; A61B 17/863; A61B 17/8615; A61B 17/862; A61B 17/7092;
(Continued)

(56) References Cited

U.S. PATENT DOCUMENTS 4,858,601 A * 8/1989 Glisson ................ F16B 35/00
411/389
4,959,064 A 9/1990 Engelhardt
(Continued)

FOREIGN PATENT DOCUMENTS

WO 2014076157 A1 5/2014

OTHER PUBLICATIONS

International Preliminary Report corresponding to related International Patent Application No. PCT/US2021/058583, mailed May 25, 2023, 8 pages.
(Continued)

*Primary Examiner* — Tracy L Kamikawa
(74) *Attorney, Agent, or Firm* — K&L Gates LLP

(57) ABSTRACT

A bone screw is provided with a resilient component that enables a surgeon to measure the amount of compression effected by the bone screw during installation and dynamically maintain that compression across the provided bone screw during fracture healing. The provided bone screw includes a leading component, a trailing component, and a resilient component that may be compressed between the leading and trailing components and which is arranged such that the bone screw's axial rigidity is maintained. The leading and trailing components may be engaged together or independently by a driving instrument. Advancing or receding only the leading component or only the trailing component alters a compression force effected by the bone screw between two bone fragments, enabling a surgeon to set a desired compression force. A measurement tool is also provided that may be used to measure an amount of compression force effected by an installed bone screw.

20 Claims, 8 Drawing Sheets

(58) Field of Classification Search
CPC ...... A61B 2017/681; A61B 2017/8655; A61B 2090/062; A61B 2090/064; A61B 2090/065; F16B 35/005; F16B 5/02; F16B 23/0084
USPC .......................................................... 411/388
See application file for complete search history.

(56) References Cited

U.S. PATENT DOCUMENTS

| | | | |
|---|---|---|---|
| 5,743,912 A | 4/1998 | Lahille et al. | |
| 5,827,285 A * | 10/1998 | Bramlet | A61B 17/80 606/328 |
| 6,471,707 B1 | 10/2002 | Miller et al. | |
| 6,656,184 B1 | 12/2003 | White et al. | |
| 7,582,107 B2 | 9/2009 | Trail et al. | |
| 7,794,483 B2 * | 9/2010 | Capanni | A61B 17/8685 606/328 |
| 9,028,534 B2 | 5/2015 | Tipirneni et al. | |
| 9,161,793 B2 * | 10/2015 | Huebner | A61B 17/8875 |
| 9,585,703 B2 * | 3/2017 | Munday | A61B 17/7225 |
| 2006/0264954 A1 | 11/2006 | Sweeney, II et al. | |
| 2007/0270855 A1 | 11/2007 | Partin | |
| 2014/0257408 A1 | 9/2014 | Trieu et al. | |
| 2014/0296919 A1 | 10/2014 | Culbert et al. | |
| 2017/0360489 A1 | 12/2017 | Palmer et al. | |
| 2018/0092677 A1 * | 4/2018 | Peterson | A61B 17/844 |
| 2019/0192206 A1 | 6/2019 | Rippe et al. | |

OTHER PUBLICATIONS

International Search Report corresponding to related International Patent Application No. PCT/US2021/058583 mailed Feb. 7, 2022, 3 pages.

International Written Opinion corresponding to related International Patent Application No. PCT/US2021/058553 mailed Feb. 7, 2022, 13 pages.

Extended European Search Report corresponding to related European Patent Application No. 21892658.2 dated Aug. 13, 2024, 7 pages.

* cited by examiner

VARIABLE PITCH TAPERED COMPRESSING SCREW FOR DYNAMIC COMPRESSION

PRIORITY CLAIM

The present application claims priority to and the benefit of U.S. Provisional Application 63/112,425, filed Nov. 11, 2020, the entirety of which is herein incorporated by reference.

BACKGROUND

When healing bone fractures it is desirable to compress the fractures so that the fractured surfaces are pressed against one another. One typical technique for compressing a fracture is the use of bone screws to draw the fractured surfaces together and thereby optimize the healing process.

When some typical bone screws are used to secure two fragments together and the bone screw is tightened, tension in the bone screw is initially very high and the fragments are held together. However, bone is a viscoelastic material and undergoes a phenomenon known as stress relaxation immediately after torque has been applied to the bone screw. The stress relaxation response is quite pronounced and causes immediate and rapid reduction in the bone screw tension and, hence, a reduction in the force holding the fragments together. Furthermore, after some typical bone screws are tightened, and the fragment is laterally displaced (e.g., by bending), the rigidity of the bone screw can cause the surrounding bone to fail since the bone is of lower strength and stiffness than the bone screw. This can lead to fixation failure of the screw, which can lead to nonunion or an undesired union of the two fracture surfaces.

Various bone screws exist that attempt to combat stress relaxation. For example, U.S. Pat. Nos. 4,959,064 and 6,656,184 each disclose a bone screw having a spring component that helps to accommodate the stress relaxation of the bone fragments. These bone screws, however, are one-part bone screws that do not allow for adjustable compression across a fracture. Additionally, typical bone screws having a spring component are most often in tension at the spring component and lack axial rigidity, which may limit the load amount that such bone screws can handle after installation into bone and makes them susceptible to failure.

In another example, U.S. Pat. Nos. 7,582,107 and 7,794,483 each disclose two-part bone screws that allow for adjustable compression across a fracture by rotating the two parts relative to each other. These bone screws, however, are subject to stripping (e.g., if over-inserted) that may cause screw pullout or fixation failure during the fracture healing process.

In another example, U.S. Pat. No. 5,743,912 discloses a bone screw including more than one part and a coil spring damping means for procuring compression at a fracture. In this bone screw, however, the leading threaded portion and the trailing threaded portion do not rotate relative to one another, which limits the ability to adjust the amount of compression effected by the bone screw.

Accordingly, a bone screw is needed that solves at least the above drawbacks.

SUMMARY

The present disclosure provides new and innovative bone screws having a resilient component (e.g., a spring) and independently rotatable leading and trailing portions that enable a surgeon to measure and adjust the amount of compression effected by the bone screw during installation and dynamically maintain that compression across the provided bone screw during healing of a fracture.

In an example, a bone screw includes a leading component, a trailing component, and a resilient component. The leading component includes a first exteriorly threaded region and a second exteriorly threaded region. The trailing component includes a third exteriorly threaded region. The resilient component is positioned around a portion of the leading component and within the trailing component. A first end of the resilient component is attached to the leading component or the trailing component and the other of the leading component and the trailing component is configured to prevent axial movement in at least one direction of a second end of the resilient component relative to the other of the leading component and the trailing component.

In another example, a system for compressing a bone fracture includes a bone screw, a first driving component, and a second driving component. The bone screw includes a leading component, a trailing component, and a resilient component. The leading component includes a first exteriorly threaded region, a second exteriorly threaded region, and a first driver feature. The trailing component includes a third exteriorly threaded region and a second driver feature. The resilient component is positioned around a portion of the leading component and within the trailing component. A first end of the resilient component is attached to the leading component or the trailing component and the other of the leading component and the trailing component is configured to prevent axial movement in at least one direction of a second end of the resilient component relative to the other of the leading component and the trailing component. The first driving component is configured to engage the first driver feature of the leading component and the second driver feature of the trailing component. The second driving component configured to engage either only the first driver feature of the leading component or only the second driver feature of the trailing component.

In some aspects, the system may further include a measurement tool configured to measure a displacement between the leading component and the trailing component of the bone screw. The measurement tool may include a shaft including a window and a rod positioned within the shaft. The rod may include an indicator and may be configured such that it may slide within the shaft. The indicator is visible through the window of the shaft. A leading end the measurement tool's shaft may be configured to accept the first driver feature of the leading component. The measurement tool may be configured such that positioning the leading end of the shaft around the first driver feature while the rod is in an initial position causes the first driver feature to force the rod to slide within the shaft. In some instances, the measurement tool can be integrated into one or both of the first driving component and the second driving component.

In another example still, a method for compressing a bone fracture includes preparing a bone hole to receive a bone screw. The bone screw includes a leading component, a trailing component, and a resilient component. The leading component includes a first exteriorly threaded region, a second exteriorly threaded region, and a first driver feature. The trailing component includes a third exteriorly threaded region and a second driver feature. The resilient component is positioned around a portion of the leading component and within the trailing component. A first end of the resilient component is attached to the leading component or the trailing component and the other of the leading component and the trailing component is configured to prevent axial movement in at least one direction of a second end of the resilient component relative to the other of the leading component and the trailing component. The bone screw may be inserted into the prepared bone hole via a first driving component configured to engage both the first driver feature of the leading component and the second driver feature of the trailing component. A compression force effected by the inserted bone screw can be measured. The compression force effected by the inserted bone screw can be adjusted via a second driving component configured to engage either only the first driver feature of the leading component or only the second driver feature of the trailing component.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

Figure 1A:
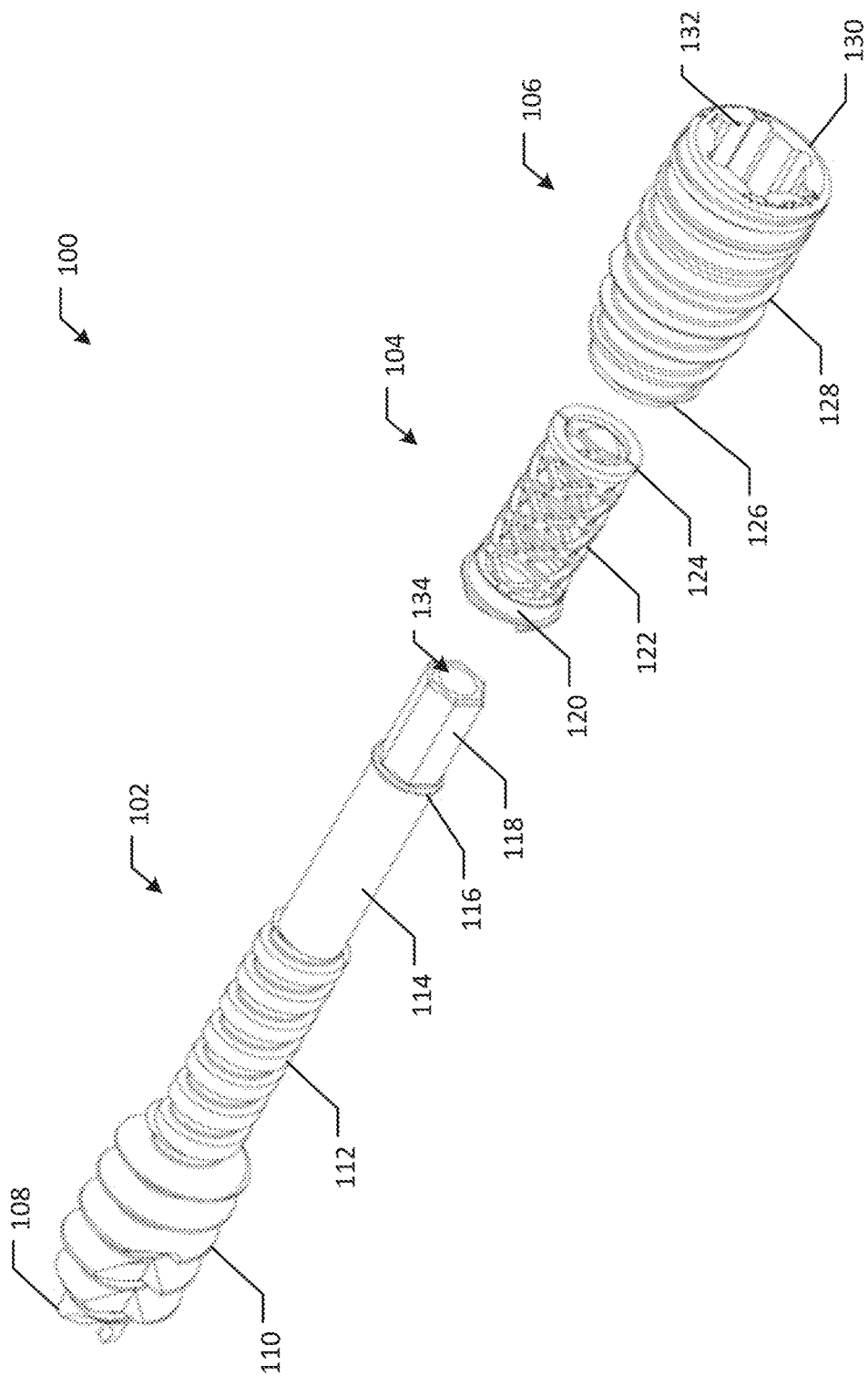
FIG. 1A illustrates an exploded view of a bone screw, according to an aspect of the present disclosure.

The present disclosure provides a bone screw with a spring component that enables a surgeon to measure the amount of compression effected by the bone screw during installation and dynamically maintain that compression across the provided bone screw during healing of a fracture. The provided bone screw includes a leading component, a trailing component, and a spring component that may be compressed between the leading component and the trailing component. The leading component and the trailing component are each constructed so as to effect compression between two boney structures when installed in bone. For example, the leading component may include two separate exteriorly threaded regions that have variable pitch threading and/or the trailing component may include a tapered body having constant pitch exterior threading.

The spring component may be positioned around a non-threaded region of the leading component and within the trailing component. The spring component may be attached to one of the leading component or the trailing component and be merely in contact with a surface of the other. This configuration enables the leading component and the trailing component to rotate relative to one another without twisting the spring component. When the provided bone screw is installed in bone, and the leading component or the trailing component is advanced or receded within the bone, the relative displacement between the leading component and the trailing component is altered. The altered relative displacement between the leading component and the trailing component causes an increase or decrease in the compression of the spring component. Accordingly, a compression force effected by the provided bone screw can be adjusted by advancing or receding either the leading component or the trailing component in bone. The adjustable compression force enables a surgeon to set a desired compression force across a fracture.

The active spring component additionally creates dynamic compression that helps enable the desired compression force to be maintained across the fracture during healing. For instance, the spring component's flexibility helps prevent or reduce the occurrences of screw stripping, pullout or failure that may occur with at least some typical bone screws when the fracture location is stressed. An advantage of the presently disclosed bone screw is that it provides the benefits of an active spring component while also maintaining the bone screw's axial rigidity, since the spring component is positioned around the leading component. The maintained axial rigidity helps the provided bone screw withstand greater loads when installed in bone as compared to at least some typical bone screws having a spring component.

In order to adjust the compression that the provided bone screw effects, the bone screw may be used with driving components particularly adapted for the provided bone screw. For example, a first driving component may be adapted to engage both a driver feature of the leading component and a driver feature of the trailing component at the same time so that both the leading and trailing components can be rotated together and be advanced or receded in bone together. This first driving component may be used to initially insert the bone screw and adjust the bone screw as a whole if needed. A second driving component may be adapted to engage only the leading component's driver feature or only the trailing component's driver feature so that only one component is rotated to the exclusion of the other. This second driving component enables altering the relative displacement between the leading component and the trailing component in bone and therefore may be used to adjust the compression force effected by the bone screw. In some instances, a third driving component may be adapted to engage the other of the leading component's driver feature or the trailing component's driver feature than the second driving component.

The present disclosure also provides a measurement tool that may be used to measure an amount of compression force effected by an installed bone screw. The provided measurement tool measures a displacement between the leading component and trailing component. This displacement may be converted to a compression force based on a spring constant of the spring component. In combination, the provided bone screw, driving components, and measurement tool enable a surgeon to set a desired compression force across a fracture for healing. Additional advantages of the provided bone screw, driving components, and/or measurement tool will be apparent from the following description of the figures.

Reference is made herein to a surgeon. It should be appreciated that a surgeon may alternatively be any other suitable healthcare professional or other user of the provided bone screw and systems.

Figure 1B:
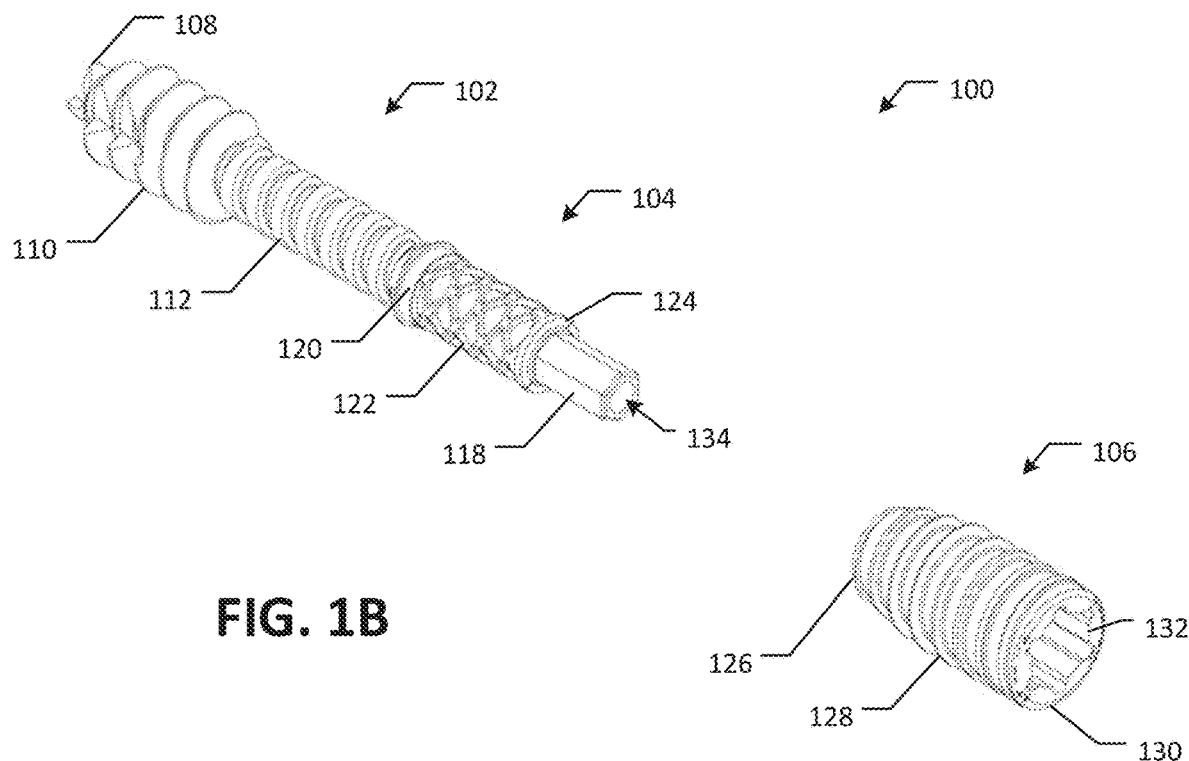
FIG. 1B illustrates a partial exploded view of the bone screw of FIG. 1A, according to an aspect of the present disclosure.
Figure 1C:
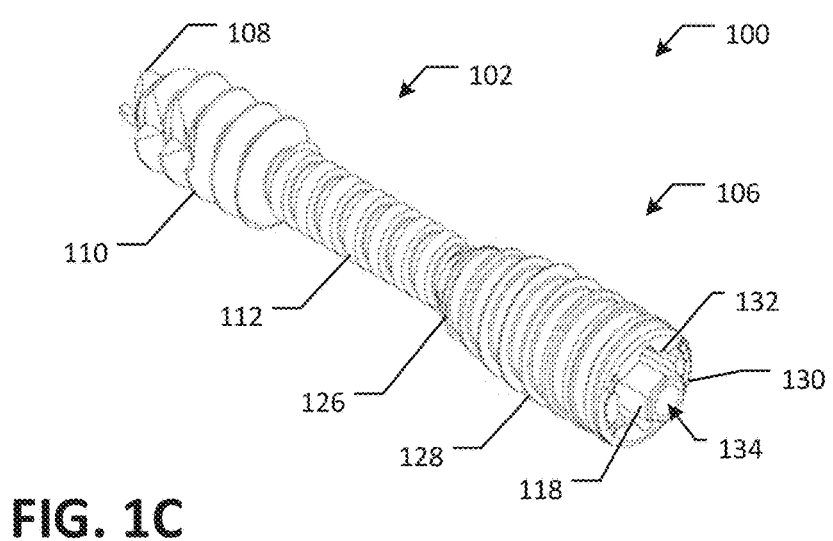
FIG. 1C illustrates a perspective view of the bone screw of FIGS. 1A and 1B, according to an aspect of the present disclosure.

FIGS. 1A to 1C illustrate an example bone screw 100. In at least some aspects, the bone screw 100 includes a leading component 102, a spring component 104, and a trailing component 106. The components of the bone screw 100 may be adapted to effect compression across a fracture when the bone screw 100 is installed in bone across the fracture. FIG. 1A illustrates an exploded view of the bone screw 100 showing each of the leading component 102, the spring component 104, and the trailing component 106 separately. In at least some aspects, the leading component 102 includes a shaft having a cutting tip 108 at its distal end. In various examples, the cutting tip 108 may be self-cutting. In at least some aspects, the shaft of the leading component 102 may be cannulated, as shown by the channel 134 in the illustrated aspect.

In at least some aspects, the shaft of the leading component 102 includes exterior threading that contributes to effecting compression between two bone fragments. For example, the leading component 102 may include an exteriorly threaded region 110. In some instances, the leading component 102 may include an exteriorly threaded region 112. The threads in the exteriorly threaded region 110 and/or the exteriorly threaded region 112 may have a variable pitch in various instances. In an example, the pitch of the exterior threads of the leading component 102 may be greatest nearest the distal end (e.g., the cutting tip 108) of the leading component 102 and may decrease moving away from the distal end through the exteriorly threaded region 110 and the exteriorly threaded region 112. The pitch of the exterior threads is measured between corresponding points on consecutive thread crests. In another example, the crest radius of the exterior threads of the leading component 102 may be greatest nearest the distal end of the leading component 102. For instance, the threads in the exteriorly threaded region 110 may have a greater crest radius than the threads in the exteriorly threaded region 112. The crest radius of the exterior threads is measured from a central axis of the leading component 102 to an outermost point on an exterior thread.

In at least some aspects, the leading component 102 may include a non-threaded region 114. For example, the non-threaded region 114 may have a smooth exterior surface. In various instances, the non-threaded region 114 terminates at a ridge 116. The ridge 116 extends outward from the exterior surface of the shaft of the leading component 102. In at least some aspects, the shaft of the leading component at its proximal end includes a driver feature 118. The driver feature 118 may have any suitable configuration that enables it to be engaged by a component of a driving instrument. In the illustrated example, the driver feature 118 has a hexagonal-shaped outer perimeter.

The spring component 104 includes a leading end 120 opposite a trailing end 124. Between the leading end 120 and the trailing end 124, the spring component 104 includes an elastic portion 122. In some aspects, such as the illustrated one, the elastic portion 122 may be a machined spring. In other aspects, the elastic portion 122 may be a coil spring or other suitable resilient elastic member. The spring component 104 may be positioned around the leading component 102, such as around the non-threaded region 114 as illustrated in FIG. 1B. The spring component 104 may be positioned within the trailing component 106 as illustrated in FIG. 1C. As discussed more below, a property of the elastic portion 122 is a spring constant which is a factor in the amount of compression force effected by the bone screw 100.

The trailing component 106 includes a body having a proximal end 126 opposite a distal end 130. The trailing component 106 is constructed to help contribute to effecting compression between two bone fragments. For instance, the body of the trailing component 106 may be tapered such that the body has a greater diameter at its distal end 130 as compared to its proximal end 126. The body of the trailing component 106 may include exterior threading 128 that has a constant pitch. In at least some aspects, the trailing component 106 includes a driver feature 132 initiating at its distal end 130. The driver feature 132 may have any suitable configuration (e.g., a modified hexalobe) that enables it to be engaged by a component of a driving instrument.

In the constructed state of the bone screw 100 shown in FIG. 1C, the leading component 102 and the trailing component 106 rotate independently of one another. In at least some aspects, the spring component 104 may be attached to either the leading component 102 or the trailing component 106. For example, as best shown in FIG. 1B of the illustrated aspect, the trailing end 124 of the spring component 104 is in contact with, but is not attached to, the ridge 116 of the leading component 102. The leading end 120 of the spring component 104, on the other hand, is attached to the trailing component 106. For example, the leading end 120 of the spring component 104 may be attached to the trailing component 106 by a weld or mechanical fit. In this example aspect, once the bone screw 100 is installed in bone, the spring component 102 rotates as a pair with the trailing component 106, since they are attached to one another. The spring component 102 is able to rotate freely about the leading component 102. Conversely, rotating the leading component 102 does not rotate the spring component 102. Additionally, the ridge 116 prevents the trailing component 106 and spring component 104 attached pair from sliding off the leading component 102.

In other aspects, the trailing end 124 of the spring component 104 may be attached to the leading component 102, such as to the ridge 116. In such other aspects, the trailing component 106 may include an interior ridge that contacts, but is not attached to, the leading end 120 of the spring component 104 (e.g., similar to the ridge 116 in the illustrated aspect). Additionally, in such other aspects, the interior ridge prevents the trailing component 106 from sliding off the leading component 102 and spring component 104 attached pair.

Figure 2A:
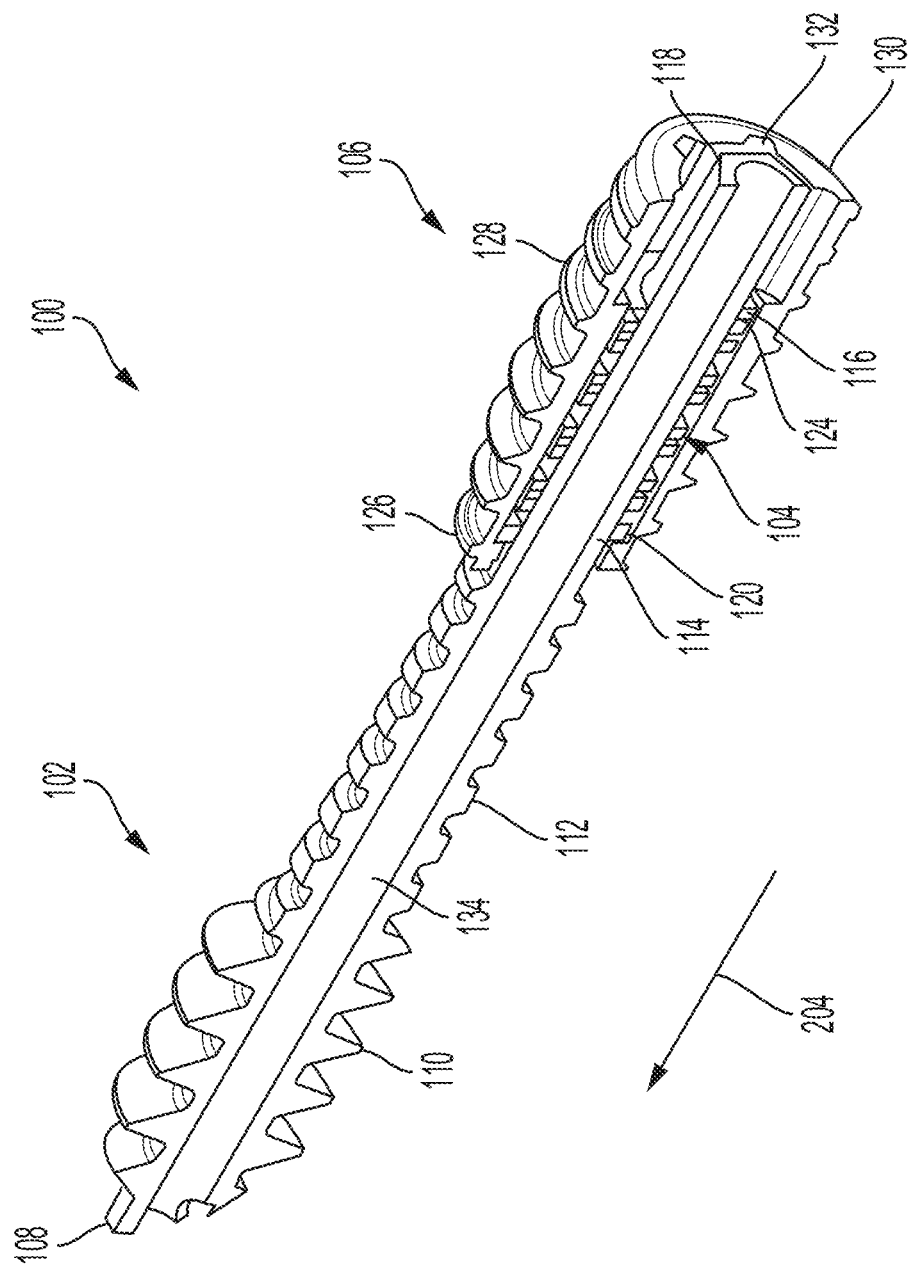
FIG. 2A illustrates a cross section of the bone screw of FIG. 1C, according to an aspect of the present disclosure.
Figure 2B:
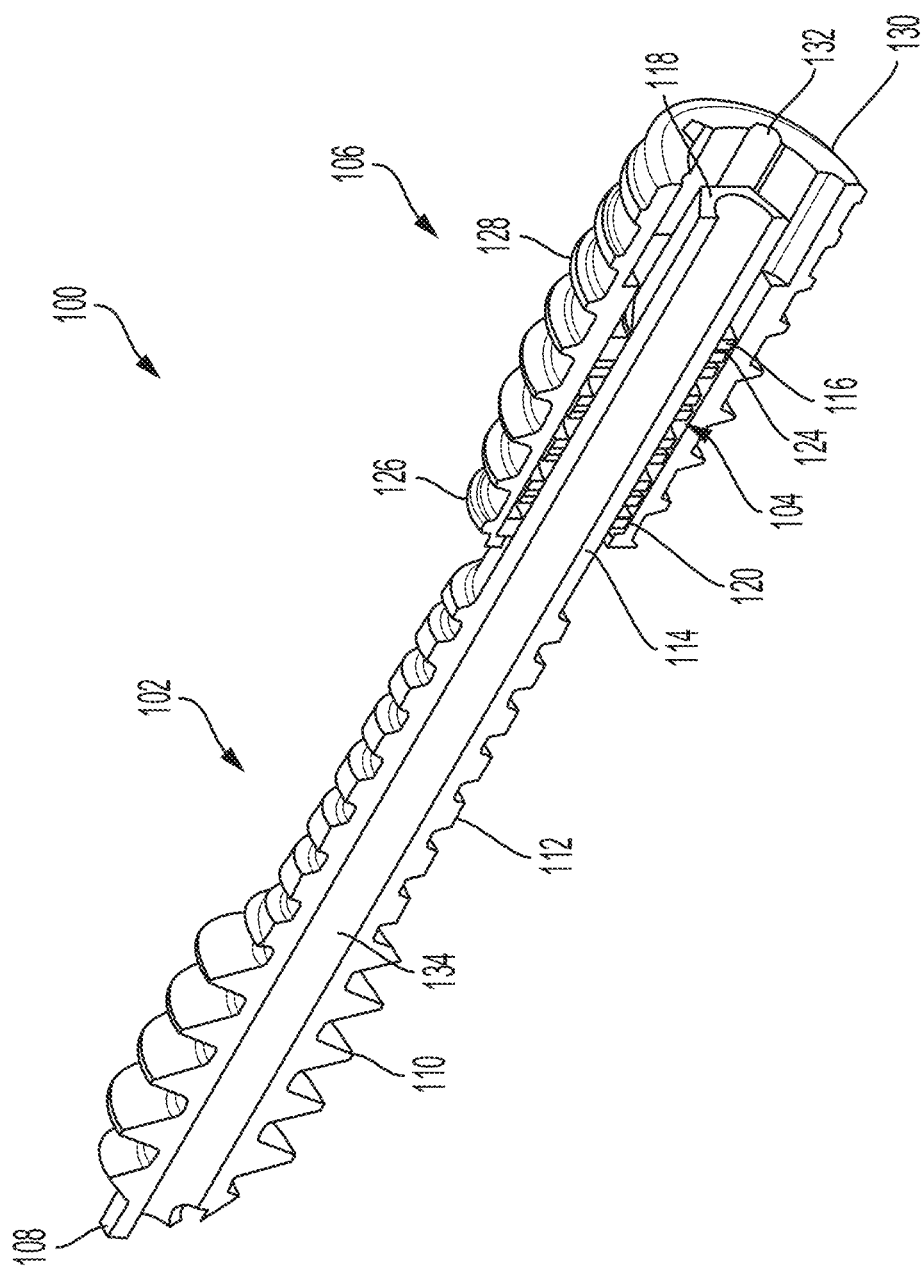
FIG. 2B illustrates a cross section of the bone screw of FIG. 2A in which the spring component is partially compressed, according to an aspect of the present disclosure.

The above-described construction of the bone screw 100 enables an adjustable amount of compression force to be effected by the bone screw 100 by enabling an adjustable relative displacement between the leading component 102 and the trailing component 104. For instance, when the bone screw 100 is installed in bone, the leading component 102 may be advanced or receded in the bone while the trailing component 106 remains stationary, or vice versa. FIG. 2A illustrates a cross section of the fully-constructed bone screw 100 shown in FIG. 1C. In an example, the leading component 102 may be advanced (e.g., via a driving instrument engaging the driver interface 118) in the direction of the arrow 204. As the leading component 102 is advanced, it compresses the spring component 104, an example result of which is illustrated in FIG. 2B. The amount that the spring component 104 is compressed, and its spring constant, are factors in the amount of compression force effected by the bone screw 100 across a fracture.

The spring component 104 additionally creates dynamic compression across a fracture that helps enable a desired compression force to be maintained across the fracture during healing. For instance, when a typical compression screw without a spring component is installed across a fracture and the fracture site is stressed (e.g., a force attempts to move the two bone fragments relative to one another), this typical compression screw has minimal, or does not have any, give and thus stress may be concentrated at the interface of the typical compression screw's threads and the bone. Repeated stresses at the fracture site may cause stripping of this typical compression screw or pullout or failure. An advantage of the bone screw 100 is that the spring component 104 provides some give that removes some of the stress from the thread and bone interface and concentrates it in the spring component 104. This helps reduce the occurrences of screw stripping, pullout or failure that may occur with the typical compression screw without a spring component. At the same time, the bone screw 100 maintains its axial rigidity and strength despite having a spring component, unlike at least some typical compression screws having a spring component, by positioning the spring component 104 around the leading component 102. The axial rigidity and strength of the bone screw 100 helps it withstand greater loads than at least some typical compression screws having a spring component.

In some aspects, the bone screw 100 may be structured to be used in the elbow, wrist, foot, or ankle to apply dynamic compression of fractures, fusions and osteotomies. The elbow, wrist, foot, and ankle include boney structures with lower bone density and therefore may benefit from a screw that has some amount of give, such as the give provided by the spring component 104 of the bone screw 100. In other aspects, the bone screw 100 may be structured to be used in the hip or shoulder. The boney structures in the hip and shoulder are larger than those in the elbow, wrist, foot, and ankle, and therefore a bone screw 100 structured for the hip or shoulder may be larger (e.g., a larger spring component 104) and have a larger dynamic range than a bone screw 100 structured for the elbow, wrist, foot, or ankle. In other aspects still, the bone screw 100 may be structured for other suitable boney structures in a patient.

In various aspects, the bone screw 100 may be constructed of a suitable biocompatible material, such as titanium, stainless steel, or nitinol. In some examples, each of the leading component 102, the spring component 104, and the trailing component 106 may be constructed from the same suitable material. In other examples, at least one of the leading component 102, the spring component 104, or the trailing component 106 may be constructed from a suitable material different than the others.

Figure 3:
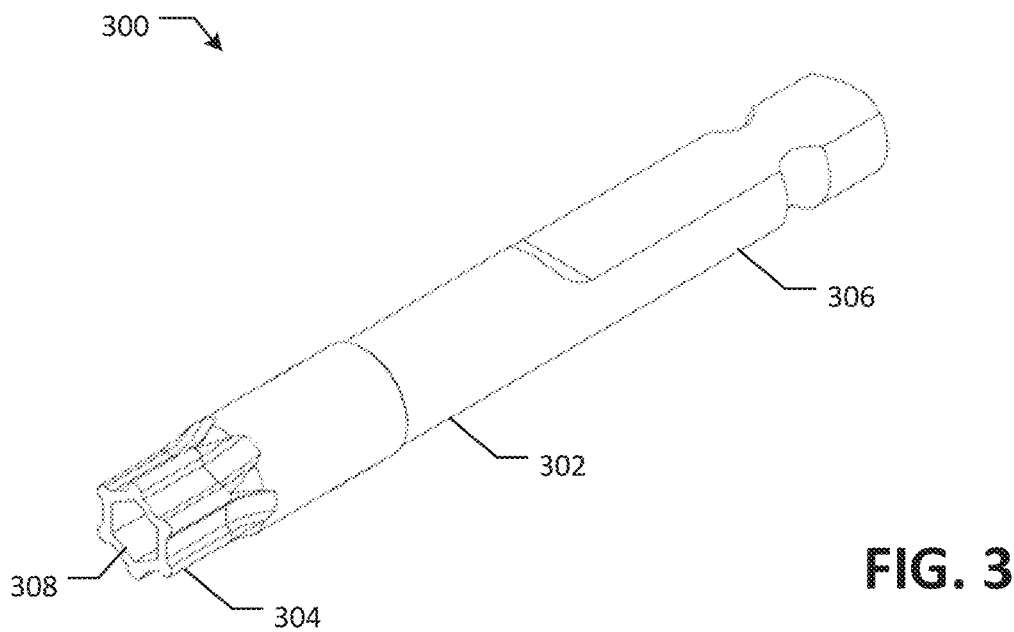
FIG. 3 illustrates a perspective view of a driver component for a trailing threaded component, according to an aspect of the present disclosure.

As described above, the leading component 102 or the trailing component 106 of the bone screw 100 may be advanced or receded in bone independently of the other. To do so, driving components may be provided that are adapted for the leading and trailing components 102 and 104 of the bone screw 100. FIG. 3 illustrates a perspective view of an example driving component 300. The driving component 300 includes a shaft 302. It should be appreciated that the shaft 302 may be any suitable length and might not be illustrated to scale. In some aspects, a trailing end 306 of the shaft 302 of the driving component 300 is adapted to connect to a driver or handle (e.g., for manual driving). For example, the trailing end 306 may be an AO connector as illustrated. In other aspects, the trailing end 306 of the shaft 302 may be integrally connected to a driver or handle. The driving component 300 may be constructed of a suitable biocompatible material.

In the illustrated example, the driving component 300 is constructed to engage both the driver interface 118 of the leading component 102 and the driver interface 132 of the trailing component 106 at the same time. For instance, the driving interface 304 is constructed to engage the driver interface 132 of the trailing component 106 and the driving interface 308 is constructed to engage the driver interface 118 of the leading component 102. The driving component 300 may be positioned around the driver interface 118 and within the driver interface 132. Engaging both the driver interface 118 of the leading component 102 and the driver interface 132 of the trailing component 106 at the same time enables a surgeon to advance the bone screw 100 as a whole into bone via the driving component 300. For example, this may be done during initial insertion of the bone screw 100.

Figure 4:
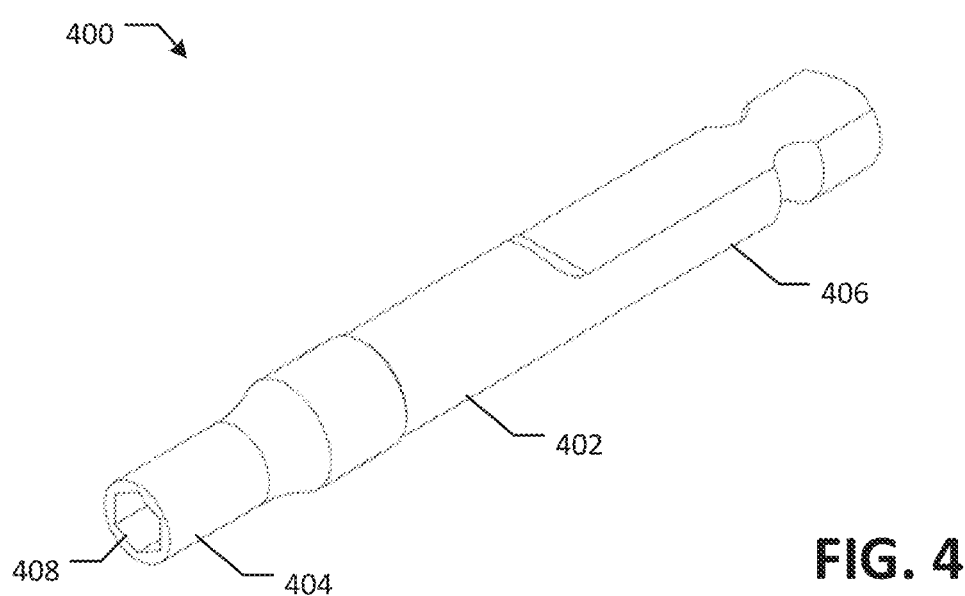
FIG. 4 illustrates a perspective view of a driver component for a leading threaded component, according to an aspect of the present disclosure.

FIG. 4 illustrates a perspective view of an example driving component 400. The driving component 400 includes a shaft 402. It should be appreciated that the shaft 402 may be any suitable length and might not be illustrated to scale. In some aspects, a trailing end 406 of the shaft 402 of the driving component 400 is adapted to connect to a driver or a handle (e.g., for manual driving). For example, the trailing end 406 may be an AO connector as illustrated. In other aspects, the trailing end 406 of the shaft 402 may be integrally connected to a driver or a handle. The driving component 400 may be constructed of a suitable biocompatible material.

In the illustrated example, the driving component 400 is constructed to engage only the driver interface 118 of the leading component 102. For instance, the driving interface 408 is constructed to engage, and corresponds to, the driver interface 118 of the leading component 102. The driving component 400 may be positioned around the driver interface 118 and within the driver interface 132. The interface 404, however, does not correspond to the driver interface 132 of the trailing component 106 and therefore does not engage the driver interface 132. In some aspects, the interface 404 may be smooth as illustrated. Engaging only the driver interface 118 of the leading component 102 enables a surgeon to advance or recede only the leading component 102 via the driving component 400. For example, the surgeon may advance or recede only the leading component 102 in order to adjust the compression force affected by the bone screw 100.

In some aspects of the present disclosure, though not illustrated, a driving component may be provided that is constructed to engage only the driver interface 132 of the trailing component 106. For example, in some instances, the interface 404 of the driving component 400 may be constructed such that it may engage, and corresponds to, the driver interface 132 of the trailing component 106 while the driving interface 408 may be constructed such that it does not correspond to, and therefore does not engage, the driver interface 118 of the leading component 102. Engaging only the driver interface 132 of the trailing component 106 enables a surgeon to advance or recede only the trailing component 106. For example, the surgeon may advance or recede only the trailing component 106 in order to adjust the compression force affected by the bone screw 100.

Figure 5A:
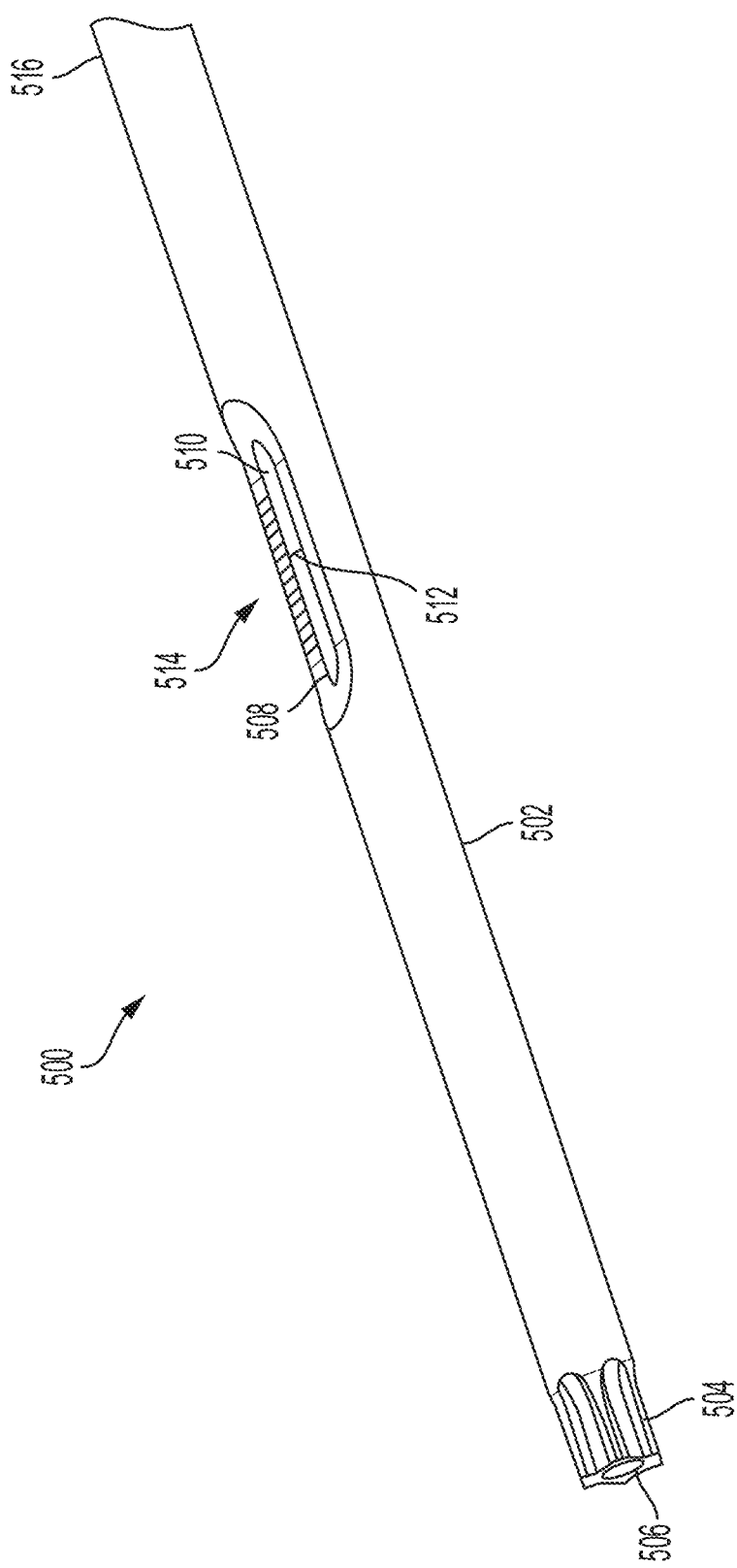
FIG. 5A illustrates a perspective view of a compression measurement tool, according to an aspect of the present disclosure.

In at least some instances, it is helpful for a surgeon to know how much compression force is applied across a fracture by a bone screw (e.g., the bone screw 100). For example, with this information, the surgeon may adjust the leading component 102 or the trailing component 106 of the bone screw 100 to achieve a desired amount of compression force across the fracture. FIG. 5A illustrates an example measurement tool 500 for measuring compression force effected by a bone screw (e.g., the bone screw 100) across a fracture. The measurement tool 500 includes a shaft 502. The trailing end 516 of the shaft 502 may form any suitable end of the measurement tool 500, such as a handle.

Figure 5B:
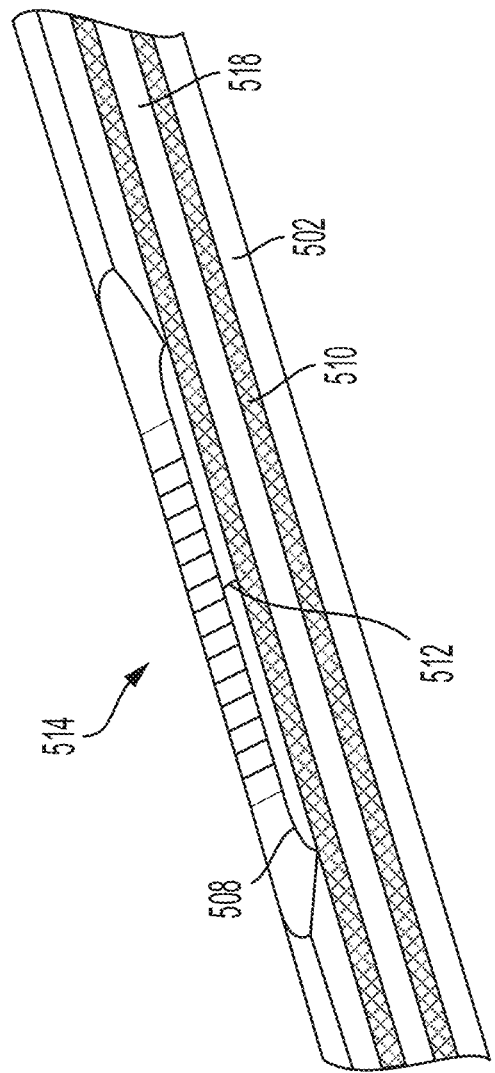
FIG. 5B illustrates a magnified cross sectional view of a measurement window of the compression measurement tool of FIG. 5A, according to an aspect of the present disclosure.

In various aspects, a rod 510 is positioned within the shaft 502. In such aspects, the rod 510 may slide within the shaft 502. In some examples, the rod 510 may be cannulated such that it includes a channel 518 (FIG. 5B). A leading end of the shaft 502 includes an interface 504 and an interface 506. In at least some aspects, the interface 506 is constructed to correspond to the driver interface 118 and/or the interface 504 is constructed to correspond to the driver interface 132. This construction of the interface 504 and/or the interface 506 helps the measurement tool 500 remain in axial alignment with the bone screw 100 to achieve accurate measurements. In an initial position, prior to a measurement being taken, the rod 510 may be positioned towards the leading end of the shaft 502. For example, an end of the rod 510 may be flush with the leading end of the shaft 510.

To take a measurement, the measurement tool 500 may be placed around the leading component 102 (e.g., the driver interface 118) and within the trailing component 106 (e.g., the driver interface 132) of the bone screw 100 such that the driver interface 118 is within the interface 506 of the measurement tool 500. In at least some aspects, the measurement tool 500 may be advanced into the trailing component 106 as far as the measurement tool 500 can be advanced. As this is done, the driver interface 118 of the trailing component 106 forces the rod 510 to slide within the shaft 502 of the measurement tool 500. In at least some aspects, the rod 510 includes an indicator 512, such as a line marking. In various aspects, the shaft 502 may include a window 508 through which the indicator 512 on the rod 510 is visible. In at least some examples, the shaft 502 includes a scale 514 adjacent to the window 508. A measurement corresponds to where the indicator 512 lines up on the scale 514. In at least some aspects, the measurement tool 500 measures a displacement between the leading component 102 and the trailing component 106 of the bone screw 100. This displacement can be converted into an amount of compression force based on a spring constant of the spring component 104. In some aspects, the scale 514 may include displacement values (e.g., millimeters). In other aspects, the scale 514 may include compression force values (e.g., Newtons).

In some aspects of the present disclosure, the measurement tool 500 may be its own separate component. In such aspects, a surgeon may take measurements with the measurement tool 500 when needed and use a separate driving component (e.g., the driving components 300 and 400) to install or adjust the bone screw 100. In other aspects of the present disclosure, the measurement tool 500 may be integrated with a driving component. For example, in such aspects, the measurement tool 500 may be constructed of one or more materials suitable to act as a driving component. Additionally, in such other aspects, a surgeon may install or adjust the bone screw 100 and take measurements with the same tool.

Figure 6:
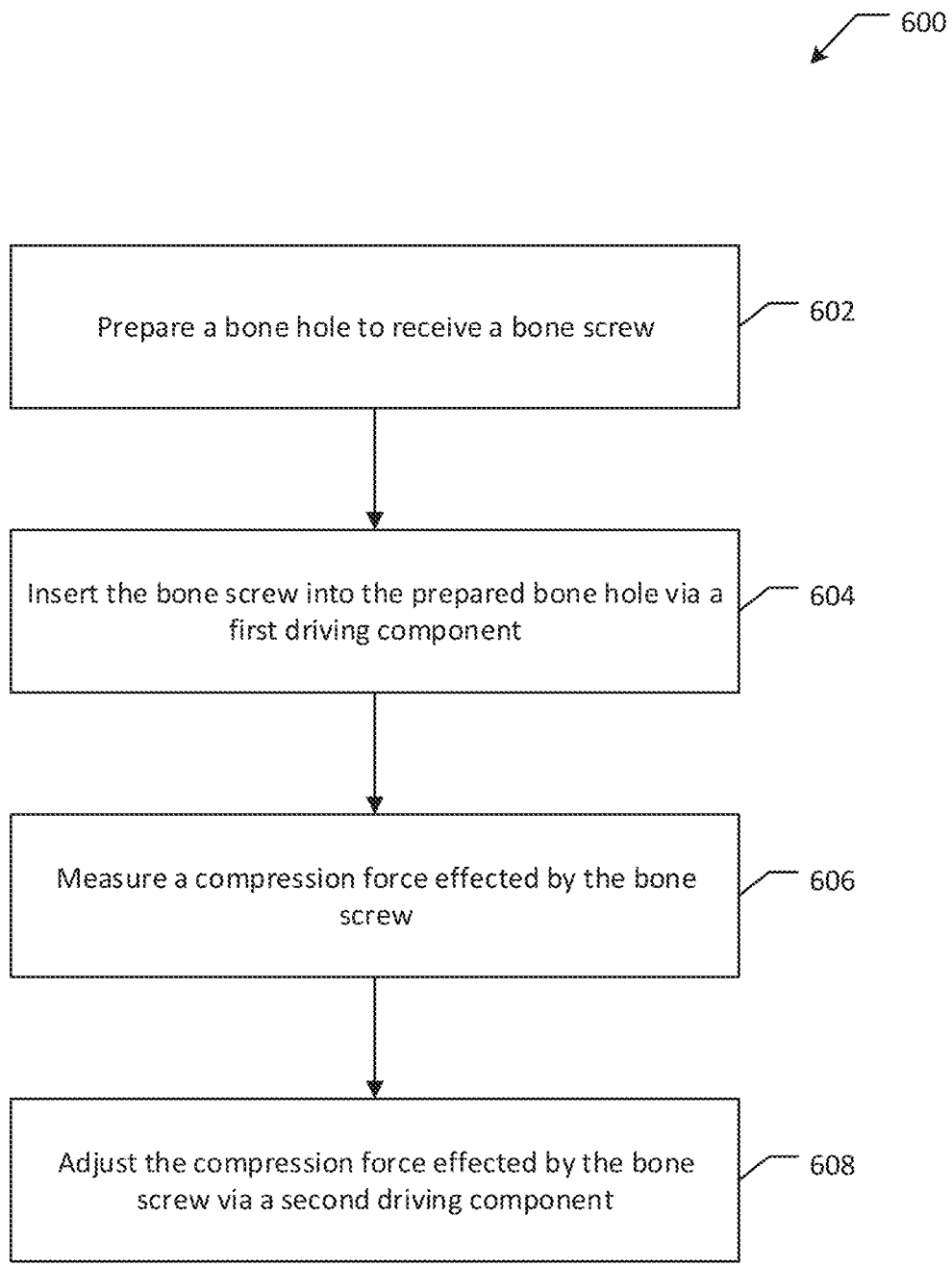
FIG. 6 illustrates a flow chart of an example method for compressing a bone fracture, according to an aspect of the present disclosure.

FIG. 6 shows a flow chart of an example method for compressing a bone fracture, according to an aspect of the present disclosure. Although the example method 600 is described with reference to the flow chart illustrated in FIG. 6, it will be appreciated that many other methods of performing the acts associated with the method 600 may be used. For example, the order of some of the blocks may be changed, certain blocks may be combined with other blocks, and some of the blocks described are optional.

In some instances, the method 600 may begin by preparing a bone hole to receive a bone screw (e.g., the bone screw 100) (block 602). In some aspects, preparing the bone hole includes inserting a guidewire at the intended location for the bone screw 100. A first drill or drill component may be used to create a hole in the bone (e.g., in the proximal cortex) having a profile similar to a posterior section (e.g., the trailing component 106) of the bone screw 100. A second drill or drill component may be used to create a hole in the bone having a profile similar to an anterior section (e.g., the leading component 102) of the bone screw 100. In at least some aspects, once the bone hole is prepared to receive the bone screw 100, a desired length and/or diameter of the bone screw 100 is determined using radiographic imaging and/or a measurement instrument. A surgeon may then choose a bone screw 100 having the determined length and/or diameter.

In at least some aspects, the surgeon may insert the chosen bone screw 100 into the prepared bone hole via a first driving component (e.g., the driving component 300) (block 604). The driving component 300 engages both the leading component 102 (e.g., the driver interface 118) and the trailing component 106 (e.g., the driver interface 132) at the same time to enable the surgeon to advance the bone screw 100 as a whole into the bone hole. The surgeon may advance the bone screw 100 to a desired position across a fracture between two bone fragments.

In various instances, the surgeon may then measure a compression force effected by the inserted bone screw 100 (block 606). For example, the surgeon may use the measurement tool 500 to measure the compression force effected by the inserted bone screw 100. In some instances, the compression force effected by the inserted bone screw 100 may be adjusted via a second driving component (e.g., the driving component 400) (bock 608). For example, the measured compression force might not be equal to a compression force that the surgeon desires for healing a particular fracture. In this example, the driving component 400 engages only the leading component 102 (e.g., the driver interface 118) to enable the surgeon to advance or recede only the leading component 102. Doing so alters the relative displacement between the leading component 102 and the trailing component 106, which adjusts the compression force effected by the bone screw 100 across the fracture. In other examples, a driving component may be used that engages only the trailing component 106 (e.g., the driver interface 132), as described above, to adjust the compression force in a similar manner.

In some instances, after adjusting the compression force, the surgeon may again measure the compression force effected by the bone screw 100. If the measured compression force is not the surgeon's desire compression force, then the surgeon may again adjust the compression force via a driving component that engages only the leading component 102 or only the trailing component 106. As described above, in some aspects, the surgeon may adjust the compression force and measure the compression force using the same tool or driving component. Once the surgeon is satisfied with the compression force effected by the bone screw 100 across the fracture, the bone screw 100 is set and the fracture is allowed to heal.

The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A bone screw comprising:
a leading component including a first exteriorly threaded region and a second exteriorly threaded region;
a trailing component including a third exteriorly threaded region; and
a resilient component positioned around a portion of the leading component and within the trailing component,
wherein a first end of the resilient component is fixedly attached to one of the leading component or the trailing component when the resilient component is in each of a compressed state and a non-compressed state so that the resilient component rotates with the one of the leading component or the trailing component when only the one of the leading component or the trailing component is rotated relative to the other of the leading component or the trailing component, but does not rotate with the other of the leading component or the trailing component when only the other of the leading component or the trailing component is rotated relative to the one of the leading component or the trailing component, and wherein the other of the leading component or the trailing component comprises a ridge in contact with, but not fixedly attached to a second end of the resilient component when the resilient component is in the compressed state, which allows each of the leading component and the trailing component to rotate relative to one another without twisting the resilient component,
wherein the ridge is configured to prevent axial movement in at least one direction of the second end of the resilient component relative to the other of the leading component or the trailing component,
wherein the resilient component is configured to be longitudinally compressed between the leading component and the trailing component and between the first end and the second end.

2. The bone screw of claim 1, wherein the first end of the resilient component is fixedly attached to the trailing component, and the leading component includes the ridge in contact with the second end of the resilient component thereby preventing axial movement of the second end relative to the leading component in the at least one direction past the ridge.

3. The bone screw of claim 1, wherein the first and second exteriorly threaded regions have a variable pitch.

4. The bone screw of claim 1, wherein the leading component further includes an exteriorly smooth region and the portion of the leading component around which the resilient component is positioned is the exteriorly smooth region.

5. The bone screw of claim 1, wherein the resilient component is a spring.

6. The bone screw of claim 1, wherein the third exteriorly threaded region extends an entire length of a body portion of the trailing component.

7. The bone screw of claim 1, wherein the bone screw is configured such that the leading and trailing components rotate independently of one another.

8. The bone screw of claim 1, wherein the bone screw is configured such that the resilient component rotates when the trailing component rotates, but the resilient component does not rotate when only the leading component rotates.

9. The bone screw of claim 1, wherein the leading component includes a first driver feature, the trailing component includes a second driver feature, and the first driver feature is different than the second driver feature.

10. The bone screw of claim 1, wherein the bone screw is configured to apply compression across a fracture when inserted into bone across the fracture.

11. The bone screw of claim 1, wherein the bone screw is configured such that, when the bone screw is installed into bone, advancing the leading component into the bone while a position of the trailing component remains constant results in compressing the resilient component.

12. A system for compressing a bone fracture comprising:
a bone screw including:
a leading component including a first exteriorly threaded region, a second exteriorly threaded region, and a first driver feature,
a trailing component including a third exteriorly threaded region and a second driver feature, and
a resilient component positioned around a portion of the leading component and within the trailing component, wherein a first end of the resilient component is fixedly attached to one of the leading component or the trailing component when the resilient component is in each of a compressed state and a non-compressed state so that the resilient component rotates with the one of the leading component or the trailing component when only the one of the leading component or the trailing component is rotated relative to the other of the leading component or the trailing component, but does not rotate with the other of the leading component or the trailing component when only the other of the leading component or the trailing component is rotated relative to the one of the leading component or the trailing component, and wherein the other of the leading component or the trailing component comprises a ridge in contact with, but not fixedly attached to a second end of the resilient component when the resilient component is in the compressed state, which allows each of the leading component and the trailing component to rotate relative to one another without twisting the resilient component,
wherein the ridge is configured to prevent axial movement in at least one direction of the second end of the resilient component relative to the other of the leading component or the trailing component,
wherein the resilient component is configured to be longitudinally compressed between the leading component and the trailing component and between the first end and the second end;
wherein the system further comprises:

a first driving component configured to engage the first driver feature of the leading component and the second driver feature of the trailing component; and a second driving component configured to engage either only the first driver feature of the leading component or only the second driver feature of the trailing component.

13. The system of claim 12, further comprising a measurement tool configured to measure a displacement between the leading component and the trailing component of the bone screw.

14. The system of claim 13, wherein the measurement tool includes:
a shaft including a window; and
a rod positioned within the shaft and configured to slide within the shaft, the rod including an indicator,
wherein the indicator is visible through the window of the shaft.

15. The system of claim 14, wherein a leading end of the shaft of the measurement tool is configured to accept the first driver feature of the leading component.

16. The system of claim 15, wherein the measurement tool is configured such that positioning the leading end of the shaft around the first driver feature causes the first driver feature to force the rod to slide within the shaft away from an initial position.

17. The system of claim 13, wherein the measurement tool is integrated into one or both of the first driving component and the second driving component.

18. A method for compressing a bone fracture comprising:
preparing a bone hole to receive a bone screw, the bone screw including:
a leading component including a first exteriorly threaded region, a second exteriorly threaded region, and a first driver feature,
a trailing component including a third exteriorly threaded region and a second driver feature, and
a resilient component positioned around a portion of the leading component and within the trailing component, wherein a first end of the resilient component is fixedly attached to one of the leading component or the trailing component when the resilient component is in each of a compressed state and a non-compressed state so that the resilient component rotates with the one of the leading component or the trailing component when only the one of the leading component or the trailing component is rotated relative to the other of the leading component or the trailing component, but does not rotate with the other of the leading component or the trailing component when only the other of the leading component or the trailing component is rotated relative to the one of the leading component or the trailing component, and wherein the other of the leading component or the trailing component comprises a ridge in contact with, but not fixedly attached to a second end of the resilient component when the resilient component is in the compressed state, which allows each of the leading component and the trailing component to rotate relative to one another without twisting the resilient component,
wherein the ridge is configured to prevent axial movement in at least one direction of the second end of the resilient component relative to the other of the leading component or the trailing component,
wherein the resilient component is configured to be longitudinally compressed between the leading component and the trailing component and between the first end and the second end;
inserting the bone screw into the prepared bone hole via a first driving component configured to engage both the first driver feature of the leading component and the second driver feature of the trailing component;
measuring a compression force effected by the inserted bone screw; and
adjusting the compression force effected by the inserted bone screw via a second driving component configured to engage either only the first driver feature of the leading component or only the second driver feature of the trailing component.

19. The method of claim 18, wherein the adjusting of the compression force effected by the inserted bone screw includes advancing or receding the leading component or the trailing component within the bone hole via the second driving component.

20. The method of claim 18, wherein the bone screw is inserted over a guide wire into the prepared bone hole.

* * * * *